(12) United States Patent
Yamamoto (10) Patent No.: US 8,915,844 B2
(45) Date of Patent: Dec. 23, 2014

(54) ENDOSCOPE DIAGNOSTIC APPARATUS (75) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 126 days.

(21) Appl. No.: 13/596,867

(22) Filed: Aug. 28, 2012

(65) Prior Publication Data
US 2013/0053646 A1 Feb. 28, 2013

(30) Foreign Application Priority Data

Aug. 29, 2011 (JP) ................................. P2011-186346

(51) Int. Cl.
*A61B 1/06* (2006.01)
*A61B 1/04* (2006.01)
*A61B 1/05* (2006.01)
*A61B 1/00* (2006.01)

(52) U.S. Cl.
CPC ................. *A61B 1/043* (2013.01); *A61B 1/063* (2013.01); *A61B 1/05* (2013.01); *A61B 1/0653* (2013.01); *A61B 1/00009* (2013.01); *A61B 1/00006* (2013.01); *A61B 1/0638* (2013.01)
USPC ............................ 600/180; 600/160; 600/178

(58) Field of Classification Search
CPC .... A61B 1/0638; A61B 1/0684; A61B 1/043; A61B 1/0646; A61B 1/00009; A61B 1/063; A61B 1/0669; A61B 5/0084; A61B 1/05; A61B 1/0653; A61B 5/0071; A61B 1/00186; A61B 1/07; A61B 5/0059; A61B 19/5202; A61B 1/00096; A61B 1/0661
USPC ......... 600/109, 118, 160, 178, 180–182, 407, 600/476; 348/68, 65, 48
See application file for complete search history.

(56) References Cited

U.S. PATENT DOCUMENTS 5,078,150 A * 1/1992 Hara et al. ..................... 600/476
6,008,889 A * 12/1999 Zeng et al. ...................... 356/73
(Continued)

FOREIGN PATENT DOCUMENTS

| EP | 2301416 A1 | 3/2011 |
| EP | 2452610 * | 5/2012 |
| JP | 2008-43383 A | 2/2008 |
| WO | WO 2011/004801 A1 | 1/2011 |

OTHER PUBLICATIONS

Extended European Search Report for European Application No. 12182017.7 dated Nov. 27, 2012.

*Primary Examiner* — John P Leubecker
*Assistant Examiner* — Arnaldo Torres Diaz
(74) *Attorney, Agent, or Firm* — Birch, Stewart, Kolasch & Birch, LLP (57) ABSTRACT The endoscope diagnostic apparatus includes a light source emitting white light and two or more kinds of excited light with different center wavelengths for emitting two or more kinds of self-fluorescence from a self-fluorescent material, an imaging unit which receives reflected light of white light to image a normal light image, and receives self-fluorescence emitted from the self-fluorescent material to image self-fluorescent images, and a light source control unit which has compensation coefficients for preventing emission intensity from being lowered depending on the volume of blood when the two or more kinds of excited light are absorbed by blood, and compensates the ratios of emission intensity of the two or more kinds of excited light using the calculated compensation coefficients so as to exclude the influence of absorption of light by blood in each of the two or more kinds of excited light.

19 Claims, 10 Drawing Sheets

(56) References Cited

U.S. PATENT DOCUMENTS

| | | | |
|---|---|---|---|
| 6,081,612 A * | 6/2000 | Gutkowicz-Krusin et al. | 382/128 |
| 6,293,911 B1 | 9/2001 | Imaizumi et al. | |
| 6,975,898 B2 * | 12/2005 | Seibel | 600/473 |
| 7,341,557 B2 * | 3/2008 | Cline et al. | 600/160 |
| 7,722,534 B2 * | 5/2010 | Cline et al. | 600/160 |
| 2006/0235277 A1 * | 10/2006 | Ohkubo et al. | 600/179 |
| 2006/0256191 A1 * | 11/2006 | Iketani et al. | 348/65 |
| 2007/0282169 A1 * | 12/2007 | Tsujita | 600/160 |
| 2008/0269563 A1 * | 10/2008 | Takahashi | 600/178 |
| 2009/0058999 A1 * | 3/2009 | Gono et al. | 348/71 |
| 2009/0167149 A1 * | 7/2009 | Ito | 313/501 |
| 2009/0203966 A1 * | 8/2009 | Mizuyoshi | 600/182 |
| 2009/0306478 A1 * | 12/2009 | Mizuyoshi | 600/178 |
| 2010/0280322 A1 * | 11/2010 | Mizuyoshi | 600/178 |
| 2012/0116159 A1 | 5/2012 | Mizuyoshi et al. | |

\* cited by examiner

| | NORMAL PART | LESION PART | ALLOCATION |
|---|---|---|---|
| FAD: EXCITATION 445 nm FLUORESCENT IMAGE OF G CHANNEL | BRIGHT ↗ | DARK ↗ | G |
| PORPHYRIN: EXCITATION 405 nm FLUORESCENT IMAGE OF R CHANNEL PORPHYRIN | DARK ↗ | BRIGHT ↖ | R,B |

ENDOSCOPE DIAGNOSTIC APPARATUS

BACKGROUND OF THE INVENTION

1. Field of the Invention

The present invention relates to an endoscope diagnostic apparatus which images self-fluorescence emitted from a self-fluorescent material included in a region (living body) to be observed of a subject to acquire a self-fluorescent image.

2. Description of the Related Art

An endoscope device which guides normal light (white light) emitted from a light source device to an endoscope tip portion, irradiates normal light onto a region to be observed of a subject, images reflected light to acquire a normal light image (white light image), and performs normal light observation (white light observation) has hitherto been used. Meanwhile, in recent years, an endoscope device which, in addition to normal light observation, irradiates excited light (special light) for self-fluorescent observation a region to be observed of a subject, images self-fluorescence emitted from a self-fluorescent material to acquire a self-fluorescent image (special light image), and performs self-fluorescent observation (special light observation) is utilized.

For example, JP2008-43383A describes an endoscope device which performs self-fluorescent observation.

JP2008-43383A describes a method in which, in a first fluorescence observation mode, three kinds of excited light are irradiated in order, and excited light is cut using an excited light cut filter provided on the front surface of a sensor to acquire a self-fluorescent image. The three kinds of excited light are different in wavelength, and the wavelength is optimized so as to capture self-fluorescent images of NADH, elastin, and collagen in which self-fluorescence intensity changes between a normal part and a lesion part.

Figure 9:
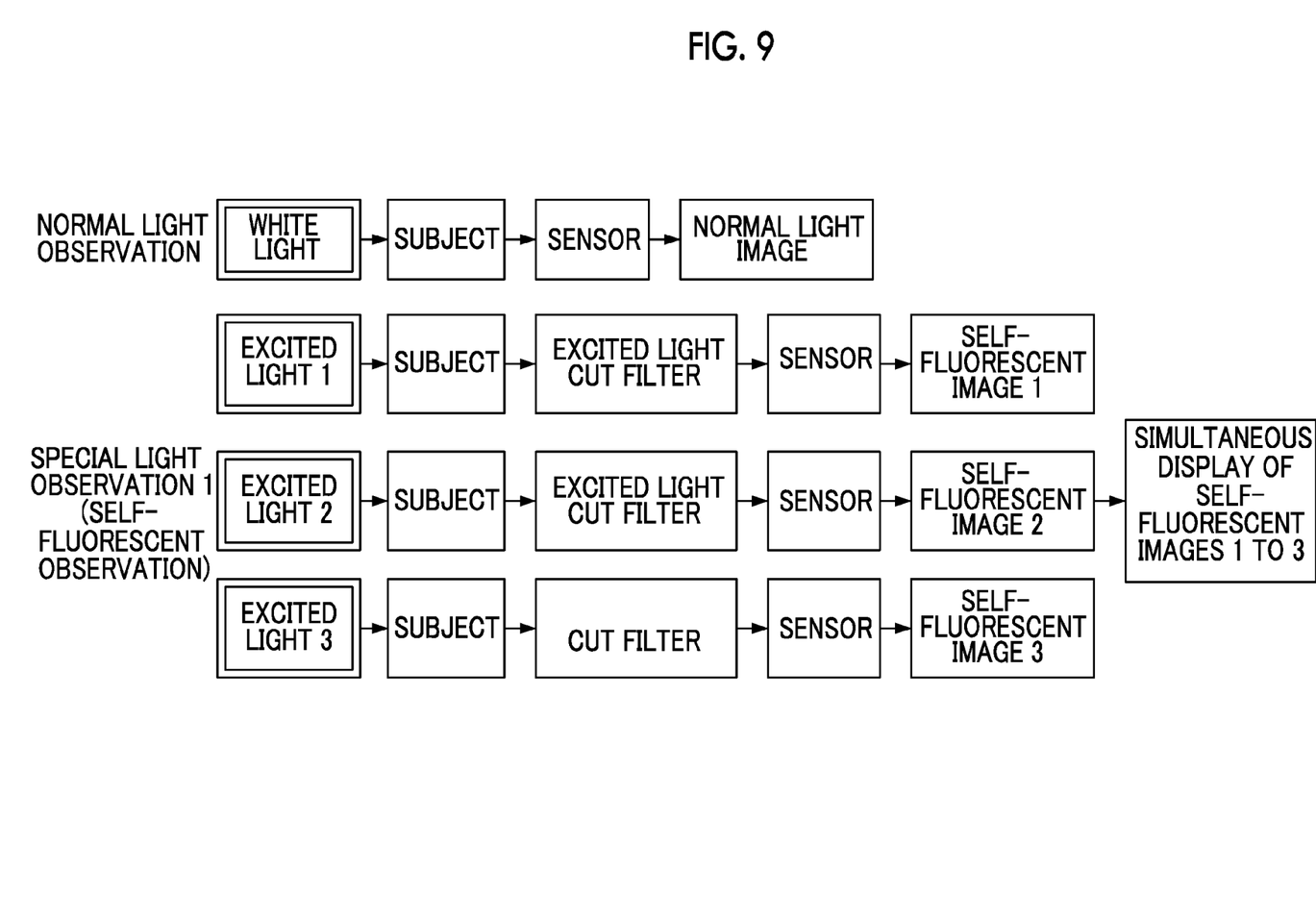
FIG. 9 is a conceptual diagram showing processing in a first fluorescence observation mode as described in JP2008-43383A.

In the first fluorescence observation mode, four fields are handled as one frame, and as shown in FIG. 9, white light, excited light 1, excited light 2, and excited light 3 are sequentially irradiated onto the subject in the respective fields of each frame. A normal light image is acquired by the sensor in the field 1, and subsequently, excited light is cut by the excited light cut filter and self-fluorescent images 1, 2, and 3 are sequentially acquired by the sensor in the fields 2 to 4. The motion images of the normal light image and the self-fluorescent images 1 to 3 are simultaneously displayed on a monitor.

JP2008-43383A describes a method in which, in a second fluorescence observation mode, two kinds of excited light 1 and 2 are irradiated in order, and these kinds of excited light 1 and 2 are cut using an excited light cut filter provided on the front surface of the sensor to acquire self-fluorescent images 1 and 2 of excited light 1 and 2, and to convert a site, at which a bright portion in the self-fluorescent image 1 and a dark portion in the self-fluorescent image 2 are aligned with each other, with a specific color to highlight a lesion part.

Figure 10:
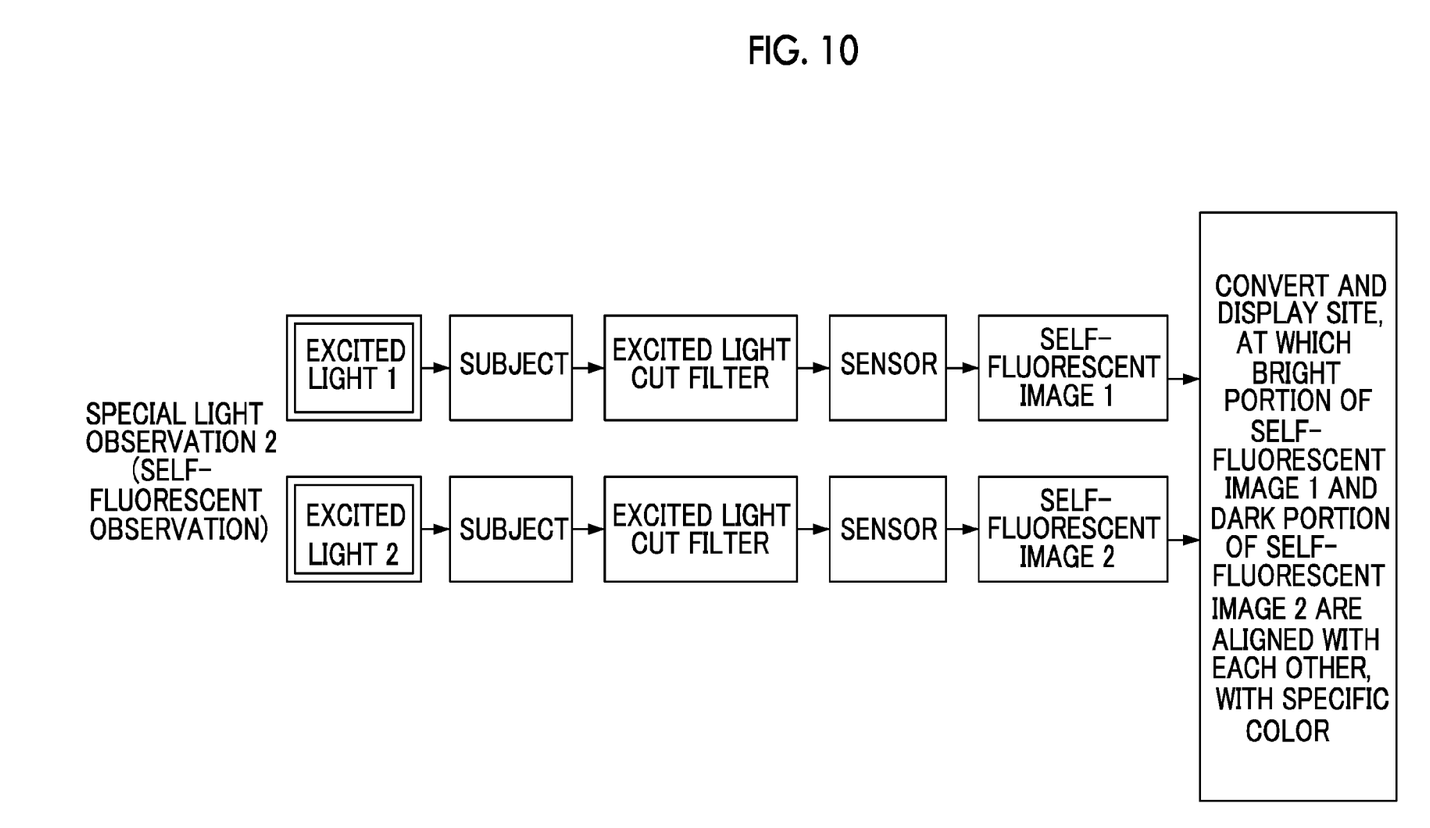
FIG. 10 is a conceptual diagram showing processing in a second fluorescence observation mode as described in JP2008-43383A.

In the second fluorescence observation mode, two fields are handled as one frame, and as shown in FIG. 10, excited light 1 and excited light 2 are alternately irradiated onto the subject in the respective fields of each frame. In the fields 1 and 2, excited light is cut by the excited light cut filter, and self-fluorescent images 1 and 2 of excited light 1 and 2 are respectively acquired by the sensor. Then, the sites of a bright portion of the self-fluorescent image 1 and a dark portion of the self-fluorescent image 2 are extracted, and the extracted sites are displayed on the monitor with a specific color.

SUMMARY OF THE INVENTION

Although in the method of JP2008-43383A, a case where a plurality of kinds of excited light with different wavelengths are irradiated in order to obtain self-fluorescent images has been described, since the degree of absorption (the amount of absorption) into blood differs depending on the wavelength of excited light, the fluorescence intensity of a self-fluorescent image to be imaged changes between when the blood volume of the subject is large and when the blood volume is small. Accordingly, as described in the second fluorescence observation mode of JP2008-43383A, the bright portion of excited light 1 and the dark portion of excited light 2 depend on the blood volume, making it difficult to discriminate a normal part and a lesion part.

An object of the present invention is to provide an endoscope diagnostic apparatus capable of obtaining self-fluorescent images with no change in fluorescence intensity depending on the blood volume of a subject.

In order to achieve the above-described object, an endoscope diagnostic apparatus according to an aspect of the present invention includes a light source unit which emits white light and two or more kinds of excited light with different center wavelengths for emitting two or more kinds of self-fluorescence from a self-fluorescent material included in a region to be observed of a subject, an imaging unit which, when white light is irradiated onto the region to be observed of the subject from the light source unit, receives reflected light of white light from the region to be observed of the subject to image a normal light image, and when two or more kinds of excited light are irradiated onto the region to be observed of the subject from the light source unit, receives self-fluorescence emitted from the self-fluorescent material included in the region to be observed of the subject to image self-fluorescent images, and a light source control unit which has compensation coefficients for preventing the fluorescence intensity of self-fluorescence generated by the two or more kinds of excited light from being lowered depending on the volume of blood when the two or more kinds of excited light emitted from the light source unit are absorbed by blood, from among the compensation coefficients, calculates compensation coefficients of the emission intensity of the two or more kinds of excited light corresponding to the image signal of the normal light image, and compensates the ratios of emission intensity of the two or more kinds of excited light using the calculated compensation coefficients so as to exclude the influence of absorption of light by blood in each of the two or more kinds of excited light.

It is preferable that the light source control unit compensates the ratios of emission intensity of the two or more kinds of excited light such that, as the image signal of the normal light image becomes smaller than a predetermined value, the emission intensity of excited light with a large amount of absorption of light by blood is greater than the emission intensity of excited light with a smaller amount of absorption of light by blood than excited light with a large amount of absorption of light by blood.

It is preferable that, when the image signal of the normal light image is greater than a predetermined value, the light source control unit performs compensation such that the ratios of emission intensity of the two or more kinds of excited light become a given identical value.

It is preferable that the light source control unit has a compensation coefficient table which stores the compensation coefficients of the emission intensity of the two or more kinds of excited light corresponding to the image signal of the normal light image, and calculates the compensation coefficients of the emission intensity of the two or more kinds of excited light corresponding to the image signal of the normal light image using the compensation coefficient table.

It is preferable that the light source unit includes first excited light with a center wavelength of 405 nm and second excited light with a center wavelength of 445 nm as the two or more kinds of excited light.

It is preferable that the light source unit includes a laser light source which emits the first excited light and the second excited light.

It is preferable that the light source control unit compensates the ratios of the emission intensity of the two or more kinds of excited light based on an image signal of green of the normal light image.

It is preferable that the imaging unit includes a first imaging element which images the normal light image, a color filter which is disposed on the optical path of the first imaging element, and has a spectral transmission characteristic for transmitting light in a wavelength range according to blue, green, and red, a second imaging element which has sensitivity higher than the first imaging element imaging the normal light image, and a filter which is disposed on the optical path of the second imaging element, and does not transmit light in the wavelength range of the two or more kinds of excited light.

According to the aspect of the present invention, the influence of absorption of light by blood can be excluded in the emission intensity of excited light, and as a result, there is no change in the fluorescence intensity of self-fluorescence depending on the blood volume of the subject, thereby obtaining self-fluorescent images in which the influence of absorption of light by blood is excluded.

DESCRIPTION OF THE PREFERRED EMBODIMENTS

Hereinafter, an endoscope diagnostic apparatus according to the present invention will be described in detail based on preferred embodiment shown in the accompanying drawings.

Figure 1:
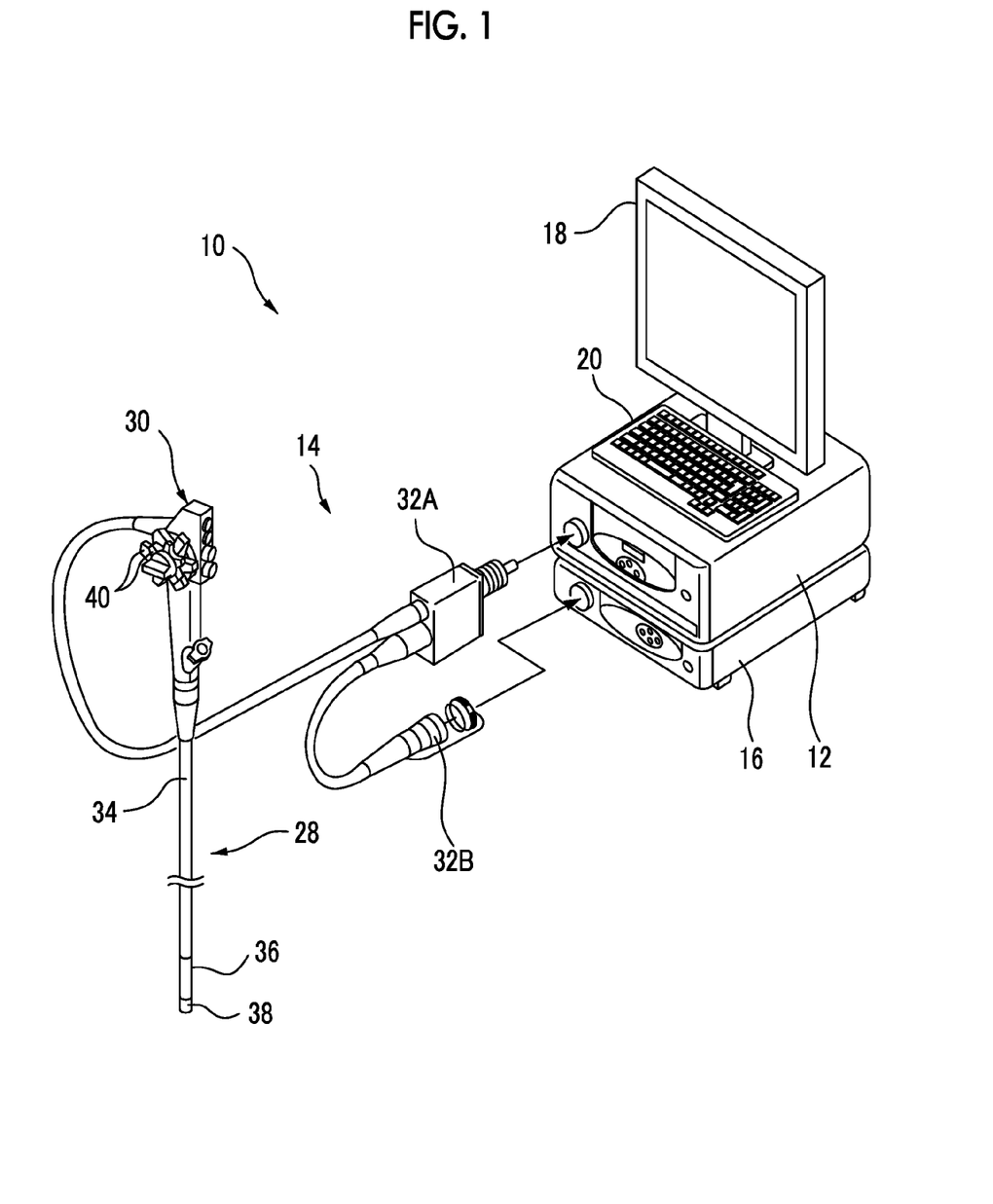
FIG. 1 is an appearance diagram showing the configuration of an endoscope diagnostic apparatus according to an embodiment of the present invention.
Figure 2:
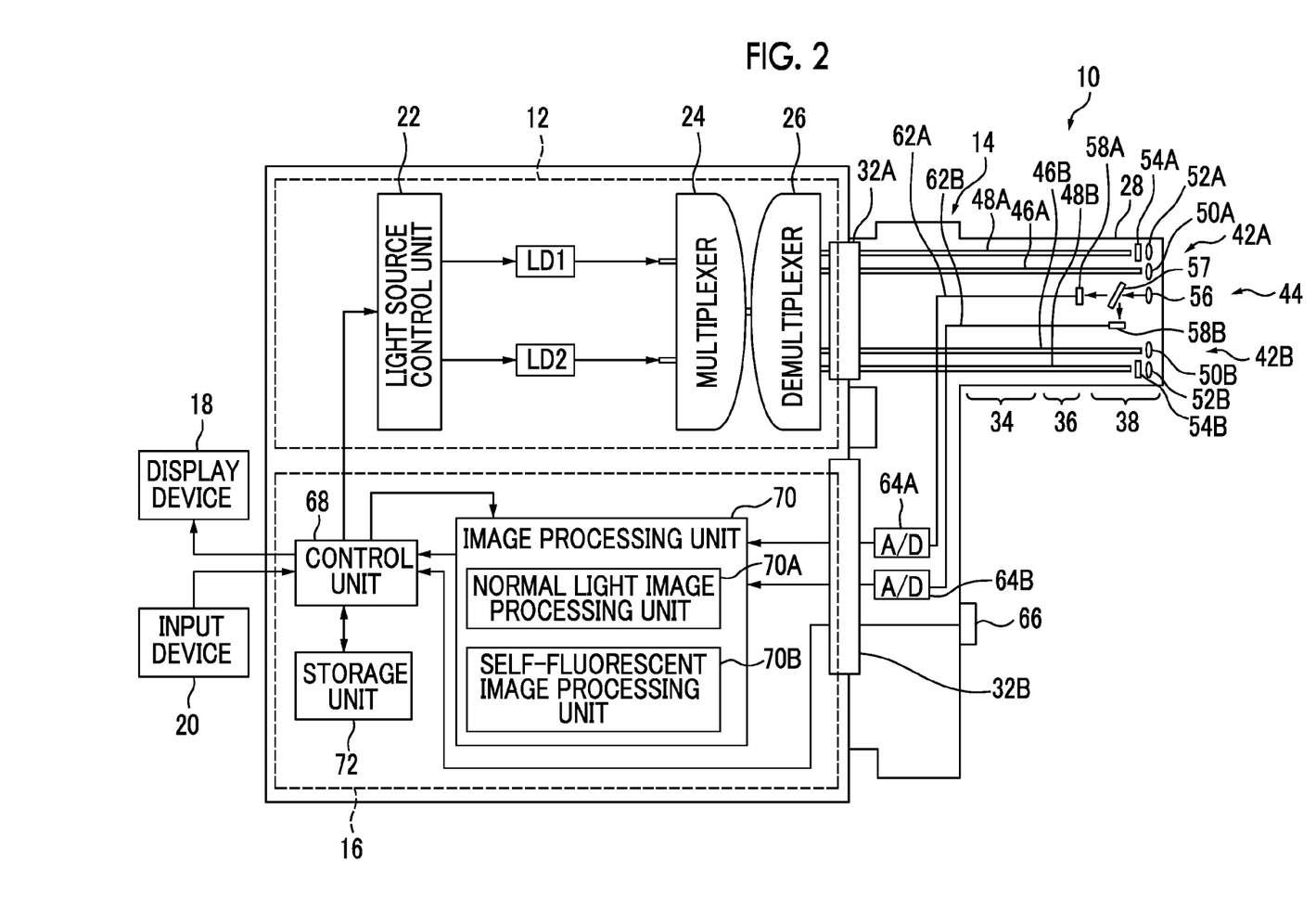
FIG. 2 is a block diagram showing the internal configuration of the endoscope diagnostic apparatus shown in FIG. 1.

FIG. 1 is an appearance diagram showing the configuration of an endoscope diagnostic apparatus according to an embodiment of the present invention. FIG. 2 is a block diagram showing the internal configuration of the endoscope diagnostic apparatus. An endoscope diagnostic apparatus 10 shown in these drawings includes a light source device 12 which generates a plurality of kinds of light with different wavelength ranges, an endoscope device 14 which guides light emitted from the light source device 12 to irradiate light onto a region to be observed of a subject, and images reflected light and self-fluorescence from the subject, a processor device 16 which performs image processing on an image imaged by the endoscope device 14 and outputs an endoscope image, a display device 18 which displays the endoscope image output from the processor device 16, and an input device 20 which receives an input operation.

The endoscope diagnostic apparatus 10 has a normal light observation mode (white light observation mode) in which normal light (white light) is irradiated onto the subject, reflected light of normal light is imaged, and a normal light image (white light image) is displayed (observed), and a self-fluorescent observation mode (special light observation mode) in which excited light (special light) for self-fluorescent observation is irradiated onto the subject, self-fluorescence is imaged, and a self-fluorescent image (special light image) is displayed. The observation modes are appropriately switched based on an instruction input from a selector switch 66 of the endoscope device 14 or the input device 20.

The light source device 12 has a light source control unit 22, two kinds of laser light sources LD1 and LD2 which emit laser light with different center wavelengths, a combiner (multiplexer) 24, and a coupler (demultiplexer) 26.

In this embodiment, narrow-band light in a predetermined wavelength range (for example, center wavelength±10 nm) from the center wavelengths of 405 nm and 445 nm are emitted from the laser light sources LD1 and LD2. The laser light sources LD1 and LD2 are light sources which irradiate emit excited light 1 and 2 for emitting self-fluorescence from a self-fluorescent material in a living body tissue, for example, porphyrin, NADH (reduced form of Nicotinamide Adenine Dinucleotide), NADPH (reduced form of Nicotinamide Adenine Dinucleotide Phosphate), FAD (Flavin Adenine Dinucleotide), or the like. As described below, the laser light source LD2 is a light source (white light source) which generates excited light for generating white light (pseudo white light) from a fluorescent substance.

The laser light sources LD1 and LD2 are individually subjected to on/off control and light quantity control by the light source control unit 22 which is controlled by a control unit of the processor device 16 described below, and the emission timing or the light quantity ratio of each of the laser light sources LD1 and LD2 is freely variable. As the laser light sources LD1 and LD2, a broad area-type InGaN-based laser diode may be used, and an InGaNAs-based laser diode, a GaNAs-based laser diode, or the like may be used.

A normal light source for generating normal light is not limited to a combination of excited light and a fluorescent substance, and any light source which emits white light may be used. For example, a Xenon lamp, a halogen lamp, a white LED (light-emitting diode), or the like may be used. An excited light source for generating excited light for self-fluorescent observation is not limited to a laser light source (semiconductor laser), and various light sources which can irradiate excited light with sufficient intensity capable of exciting a self-fluorescent material to emit self-fluorescence, for example, a combination of a white light source and a band-limiting filter or the like may be used.

The wavelength (the center wavelength or the wavelength rage of narrow-band light) of excited light for normal light observation is not particularly limited, and all kinds of excited light with a wavelength such that pseudo white light can be emitted from a fluorescent substance may be used. The wavelength of excited light for self-fluorescent observation is not particularly limited, and all kinds of excited light with a wavelength such that a self-fluorescent material is excited to emit self-fluorescence may be used. For example, light with a wavelength of 370 to 470 nm, and in particular, light with a wavelength of 400 to 450 nm may be suitably used.

Although in this embodiment, a normal light source and one of excited light sources are commonly used, both may be constituted by separate light sources. Although in this embodiment, two kinds of excited light with the center wavelengths of 405 nm and 445 nm are used as an excited light for self-fluorescent observation, the number of kinds of excited light for self-fluorescent observation is not limited to two, two or more kinds of excited light corresponding to the self-fluorescent material may be used depending on the type of self-fluorescence to be emitted.

The light source device 12 of this embodiment and a fluorescent substance constitute a light source unit of the present invention. The light source unit of the present invention emits white light and two or more kinds of excited light with different center wavelengths for emitting two or more kinds of self-fluorescence from the self-fluorescent material included in the region to be observed of the subject.

The light source control unit 22 has compensation coefficients for preventing the fluorescence intensity of self-fluorescence generated by excited light 1 and 2 from being lowered depending on the volume of blood when excited light 1 and 2 emitted from the light source unit are absorbed by blood, from among the compensation coefficients, calculates compensation coefficients a and b of the emission intensity of excited light 1 and 2 corresponding to the image signal of a G color of the normal light image, and compensates the ratios of emission intensity of excited light 1 and 2 using the calculated compensation coefficients a and b so as to exclude the influence of absorption of light by blood in each of excited light 1 and 2. The calculation of the compensation coefficients corresponding to the image signal of G color of the normal light image refers to the calculation of the compensation coefficients from the obtained image signal of G color based on the relationship (compensation coefficient table or the like) between a preset image signal of G signal and a compensation coefficient. The compensation coefficient table or the like will be described below.

The light source control unit 22 turns off the laser light source LD1 and turns on the laser light source LD2 in the normal light observation mode. In the self-fluorescent observation mode, the light source control unit 22 sequentially turns on the laser light sources LD1 and LD2 in the respective frames.

Laser light emitted from each of the laser light sources LD1 and LD2 is input to a corresponding optical fiber through a condensing lens (not shown), multiplexed by the combiner 24, demultiplexed to four-system light by the coupler 26, and transmitted to a connector portion 32A. The combiner 24 and the coupler 26 are constituted by half mirrors, reflecting mirrors, or the like. The invention is not limited thereto, and laser light may be directly sent from each of the laser light sources LD1 and LD2 to the connector portion 32A without using the combiner 24 and the coupler 26.

Subsequently, the endoscope device 14 is an electronic endoscope having an illumination optical system which emits four-system (four-lamp) light (normal light and excited light 1 and 2 for self-fluorescent observation) from the tip of the endoscope insertion portion to be inserted into the subject, and an two-system (two-lens) imaging optical system which images the endoscope image of the region to be observed. The endoscope device 14 includes an endoscope insertion portion 28, an operation unit 30 which performs a bending operation of the tip of the endoscope insertion portion 28 or an operation for observation, and connector portions 32A and 32B which detachably connect the endoscope device 14 to the light source device 12 and the processor device 16.

The endoscope insertion portion 28 has a flexible portion 34, a bending portion 36, and a tip portion (hereinafter, referred to as an endoscope tip portion) 38.

The bending portion 36 is provided between the flexible portion 34 and the tip portion 38, and is freely bendable by a rotation operation of an angle knob 40 provided in the operation unit 30. The bending portion 36 can be bent in an arbitrary direction at an arbitrary angle in accordance with a region of the subject where the endoscope device 14 is used, and can direct the endoscope tip portion 38 toward a desired region to be observed.

Though not shown, various channels, such as a forceps channel, into which a device for tissue extraction or the like is inserted, and a channel for air supply and water supply, are provided inside the operation unit 30 and the endoscope insertion portion 28.

Figure 3:
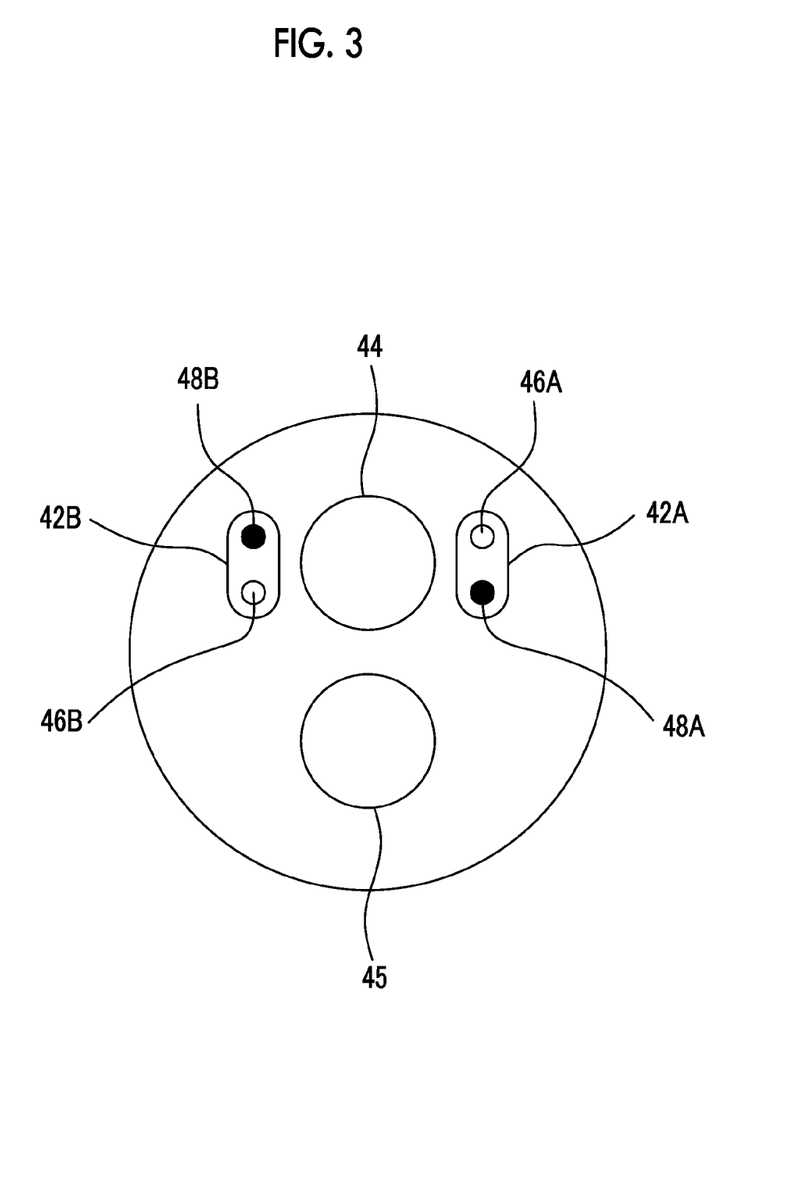
FIG. 3 is a conceptual diagram showing the state of a tip portion of an endoscope insertion portion of the endoscope diagnostic apparatus shown in FIG. 1.

As shown in FIG. 3, in the tip surface of the endoscope tip portion 38, in addition to two-system illumination windows 42A and 42B which irradiates light onto the region to be observed, and a one-system observation window 44 which images reflected light and self-fluorescence from the region to be observed, a forceps port 45 and the like are arranged.

Two-system optical fibers 46A and 48A are stored at the back of the illumination window 42A. The optical fibers 46A and 48A extend from the light source device 12 to the endoscope tip portion 38 through the connector portion 32A. An optical system, such as a lens 50A, is attached to the tip portion (the illumination window 42A side) of the optical fiber 46A. A fluorescent substance 54A is disposed in the tip portion of the optical fiber 48A, and an optical system, such as a lens 52A, is attached ahead of the fluorescent substance 54A.

Similarly, at the back of the illumination window 42B are stored two-system optical fibers of an optical fiber 46B having an optical system, such as a lens 50B, in the tip portion, and an optical fiber 48B having a fluorescent substance 54B, a lens 52B, and the like in the tip portion.

The fluorescent substances 54A and 54B include a plurality of fluorescent materials (for example, a YAG-based fluorescent material or BAM ($BaMgAl_{10}O_{17}$) which absorb a part of blue laser light from the laser light source LD2 and excites and emits green to yellow. If excited light 1 and 2 for normal light observation are irradiated onto the fluorescent substances 54A and 54B, excited and emitted light (fluorescence) of green to yellow emitted from the fluorescent substances 54A and 54B and blue laser light which transmits without being absorbed by the fluorescent substances 54A and 54B are combined, and white light (pseudo white light) is generated.

The illumination optical systems on the illumination window 42A side and the illumination window 42B side have the same configuration and action, and can prevent illumination irregularity by simultaneously irradiating illumination light from the illumination windows 42A and 42B. Different kinds of illumination light may be irradiated from the illumination windows 42A and 42B. It is not necessary to provide an illumination optical system which emits four-system illumination light, and for example, the same function may be realized by an illumination optical system which emits two-system and one-system illumination light.

An optical system, such as a lens 56, is attached at the back of the observation window 44, and a half mirror 57 is provided at the back of the lens 56. Imaging elements 58A and 58B, such as a CCD (Charge Coupled Device) image sensor or a CMOS (Complementary Metal-Oxide Semiconductor) image sensor, which acquire image information of the region to be observed are attached ahead of the optical path of a transmitted light transmitted the half mirror 57 and ahead of the optical path of reflected light reflected by the half mirror 57. The imaging element 58A (normal sensor) is for normal light observation, and the imaging element 58B (high-sensitivity sensor) is for self-fluorescent observation. Since the signal intensity (fluorescence intensity) of self-fluorescence is weak, in this embodiment, an imaging element having higher sensitivity than the imaging element 58A for normal light observation is used as the imaging element 58B for self-fluorescent observation.

The invention is not limited to the half mirror 57, and for example, a total reflection mirror may be put on the optical path of received light to distribute received light to the imaging element 58A and the imaging element 58B.

The imaging element 58A receives light (transmitted light) from the lens 56 on the light-receiving surface (imaging surface), photoelectrically converts received light, and output an imaging signal (analog signal), and has a plurality of sets of pixels arranged in a matrix, each set having a R pixel, a G pixel, and a B pixel. R, G, and B color filters which have spectral transmission characteristics to trisect reflected light in a wavelength range of about 370 to 720 nm of visible light from the region to be observed corresponding to a R pixel, a G pixel, and a B pixel are provided on the light-receiving surface of the imaging element 58A (on the optical path).

The imaging element 58B receives light (reflected light) from the lens 56 on the light-receiving surface (imaging surface), photoelectrically converts received light, and outputs an imaging signal (analog signal), and has a plurality of monochrome pixels arranged in a matrix. An excited light cut filter which as a spectral transmission characteristics to shield excited light 1 and 2 with the center wavelengths of 405 nm and 445 nm and to transmit self-fluorescence in a wavelength range of about 500 to 700 nm of R color and G color emitted from the self-fluorescent material is provided on the light-receiving surface of the imaging element 58B (on the optical path).

The imaging elements 58A and 58B of this embodiment constitutes an imaging unit of the present invention. When white light is irradiated onto the region to be observed of the subject from the light source unit, the imaging unit of the present invention receives reflected light of white light from the region to be observed of the subject to image a normal light image. When two or more kinds of excited light are irradiated onto the region to be observed of the subject from the light source unit, the imaging unit receives self-fluorescence emitted from the self-fluorescent material included in the region to be observed of the subject to image self-fluorescent images.

Light which is guided from the light source device 12 by the optical fibers 46A and 46B, and 48A and 48B is irradiated from the endoscope tip portion 38 toward the region to be observed of the subject. Reflected light from the region to be observed onto which light is irradiated or self-fluorescence emitted from the self-fluorescent material of the region to be observed is focused on the light-receiving surfaces of the imaging elements 58A and 58B by the lens 56, photoelectrically converted by the imaging elements 58A and 58B, and imaged. Imaging signals (analog signals) of the imaged region to be observed of the subject are output from the imaging elements 58A and 58B.

In the normal light observation mode, excited light for normal light observation emitted from the laser light source LD2 is guided by the optical fibers 48A and 48B and irradiated onto the fluorescent substances 54A and 54B, and white light emitted from the fluorescent substances 54A and 54B are irradiated onto the region to be observed of the subject from the illumination windows 42A and 42B. Reflected light from the region to be observed of the subject onto which white light is irradiated is condensed by the lens 56, multiplexed by the color filters, and a normal light image is imaged by the imaging element 58A.

In the self-fluorescent observation mode, excited light 1 and 2 for self-fluorescent observation sequentially emitted from the laser light sources LD1 and LD2 in the respective frames are guided by the optical fibers 46A and 46B, and irradiated from the endoscope tip portion 38 toward the region to be observed of the subject. Self-fluorescence emitted from the self-fluorescent material of the region to be observed of the subject onto which excited light 1 and 2 are irradiated is condensed by the lens 56, excited light 1 and 2 are cut by the excited light cut filter, and self-fluorescent images 1 and 2 are sequentially imaged by the imaging element 58B.

The imaging signals (analog signals) of the images (the normal light image and the self-fluorescent images) output from the imaging elements 58A and 58B are respectively input to A/D converters 64A and 64B through scope cables 62A and 62B. The A/D converters 64A and 64B respectively convert the imaging signals (analog signals) from the imaging elements 58A and 58B to image signals (digital signals). The image signals after conversion are input to an image processing unit 70 of the processor device 16 through the connector portion 32B.

Subsequently, the processor device 16 includes a control unit 68, an image processing unit 70, and a storage unit 72. The display device 18 and the input device 20 are connected to the control unit 68. The processor device 16 controls the light source control unit 22 of the light source device 12 based on an instruction input from the selector switch 66 of the endoscope device 14 or the input device 20, performs image processing on the image signals input from the endoscope device 14, generates images for display, and outputs the generated images to the display device 18.

The control unit 68 controls the operations of the image processing unit 70 and the light source control unit 22 of the light source device 12 based on an instruction from the selector switch 66 of the endoscope device 14 or the input device 20, for example, an instruction, such as an observation mode.

The image processing unit 70 performs predetermined image processing on the image signals input from the endoscope device 14 based on the observation mode in accordance with the image types of the normal light image and the self-fluorescent images under the control of the control unit 68. The image processing unit 70 includes a normal light image processing unit 70A and a self-fluorescent image processing unit 70B.

In the normal light observation mode, the normal light image processing unit 70A performs predetermined image processing suitable for a normal light image on the image signal (image data) of the normal light image supplied from the A/D converter 64A, and outputs (generates) a normal light image signal (normal light image).

In the self-fluorescent observation mode, the self-fluorescent image processing unit 70B predetermined image processing suitable for self-fluorescent images on the image signals (image data) of the self-fluorescent images supplied from the A/D converter 64B, and outputs (generates) self-fluorescent image signals (self-fluorescent images).

The image signals processed by the image processing unit 70 are sent to the control unit 68. In the control unit 68, the normal light image or a combined image of the normal light image and the self-fluorescent images is displayed on the display device 18 based on the normal light image signal and the self-fluorescent image signals in accordance with the observation mode. The control unit 68 allocates an image signal of a self-fluorescent image 2 to a G channel and allocates an image signal of a self-fluorescent image 1 to a R channel and a B channel to display the self-fluorescent images on the display device 18 in a pseudo color manner.

The normal light image signal and the self-fluorescent image signals are stored in the storage unit 72 having a memory or a storage device, for example, in terms of one (one-frame) image under the control of the control unit 68 as necessary.

Hereinafter, absorption of light by blood and a compensation method thereof will be described.

Figure 4:
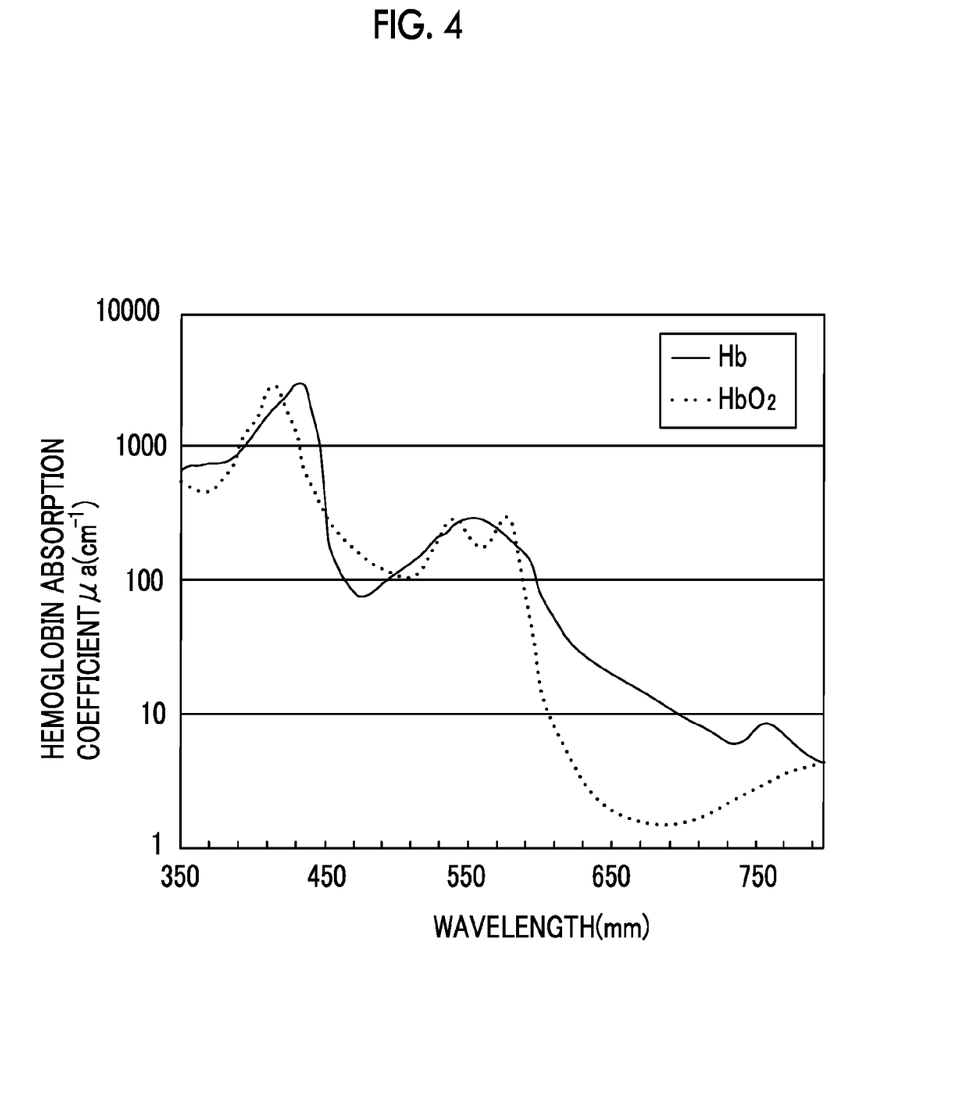
FIG. 4 is a graph showing absorption coefficients of oxidized hemoglobin and reduced hemoglobin.

FIG. 4 is a graph showing absorption coefficients of oxidized hemoglobin and reduced hemoglobin. In the graph, the vertical axis represents an absorption coefficient μa (cm$^{-1}$) of hemoglobin, and the horizontal axis represents a wavelength (nm). As shown in the graph, hemoglobin in blood has an absorption characteristic in which the absorption coefficient μa changes depending on the wavelength of light to be irradiated. The absorption coefficient μa represents absorbance which is the magnitude of absorption of light of hemoglobin. Reduced hemoglobin Hb which is not coupled oxygen and oxidized hemoglobin HbO$_2$ which is coupled to oxygen have different absorption characteristics, and have a difference in absorbance excluding an isosbestic point (in FIG. 4, the cross point of reduced hemoglobin and oxidized hemoglobin) where absorbance (absorption coefficient pa) is identical. In general, since the distribution of FIG. 4 nonlinearly changes depending on an observation-target region, it is necessary to calculate absorbance by actual measurement of a living body tissue, a light propagation simulation, or the like in advance. From the graph, it is understood that excited light 1 with a center wavelength of 405 nm and excited light 2 with a center wavelength of 445 nm for self-fluorescent observation is greatly affected by absorption of light by blood. It is also understood that excited light 1 is more greatly affected by absorption of light by blood than excited light 2.

Figure 5:
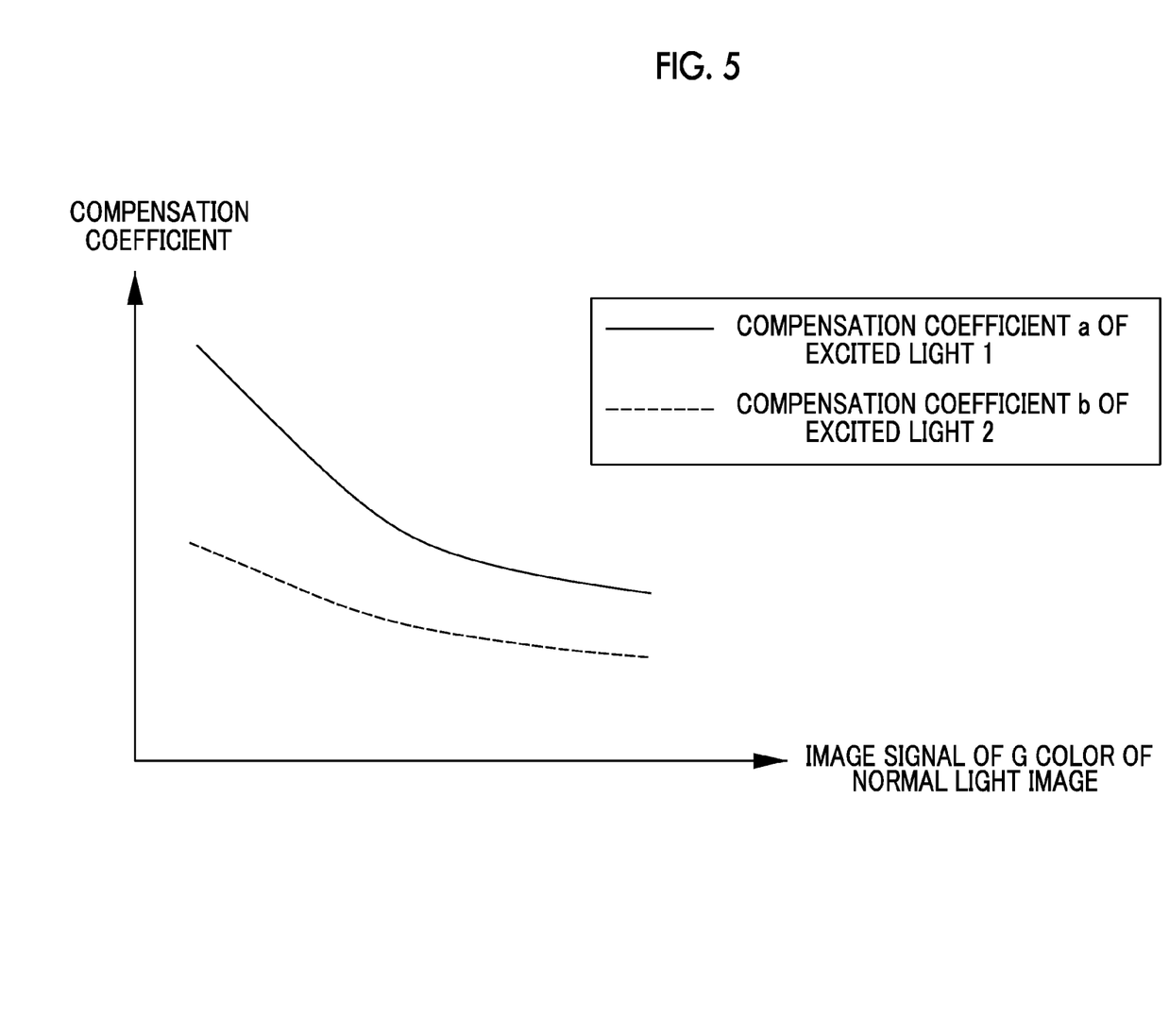
FIG. 5 is a graph showing an example of compensation coefficients for compensating for the emission intensity of excited light.

Subsequently, FIG. 5 is a graph showing an example of compensation coefficients for compensating for the emission intensity of excited light. In the graph, the vertical axis represents a compensation coefficient, and the horizontal axis represents an image signal of G color of a normal light image. The graph shows compensation coefficients a and b for preventing emission intensity from being lowered depending on the volume of blood when excited light 1 and 2 are absorbed by blood. The compensation coefficients a and b are calculated based on the image signal of G color of the normal light image in advance so as to exclude the influence of absorption of light by blood in the emission intensity of each kind of excited light 1 and 2.

When the image signal of G color of the normal light image is greater than a predetermined value, that is, when the blood volume is small, and the influence of absorption of light by blood is negligibly small, the compensation coefficients a and b are set such that the ratios of the emission intensity of excited light 1 and the emission intensity of excited light 2 are a given identical value. The ratios of the emission intensity of the compensation coefficients a and b are set such that, as the image signal of G color of the normal light image becomes smaller than the predetermined value, that is, as the blood volume increases, and the influence of absorption of light by blood non-negligibly increases, the emission intensity of excited light 1 with a great influence (amount of absorption) of absorption of light becomes larger than the emission intensity of excited light 2 with a smaller influence (amount of absorption) of absorption of light by blood than excited light 1.

The compensation coefficients a and b are calculated based on the image signal (signal intensity of reflected light) of G color of the normal light image from the relationship shown in the graph, and the emission intensity of the excited light 1 and 2 is compensated using the calculated compensation coefficients a and b. The emission intensity of excited light 1 after compensation is calculated with multiplying a reference current value 1 for driving the laser light source emitting excited light by the compensation coefficient a. Similarly, the emission intensity of excited light 2 after compensation is calculated with multiplying a reference current value 2 for driving the laser light source emitting excited light by the compensation coefficient b. Accordingly, the influence of absorption of light by blood is excluded in the emission intensity of excited light 1 and 2 after compensation, thereby obtaining self-fluorescent images in which the influence of absorption of light by blood is excluded.

As described above, excited light 1 and 2 have characteristics in which the fluorescence intensity is lowered depending on the volume of blood when excited light 1 and 2 are absorbed. Similarly, since reflected light is absorbed by blood, for example, the degree (the amount of absorption of light) of influence of absorption of light by blood is calculated from the image signal (signal intensity) of G color of the normal light image, thereby compensating the influence of absorption of light in the emission intensity of excited light 1 and 2 based on the calculated image signal of G color of the normal light image.

It is not necessary to compensate the fluorescence intensity of excited light 1 and 2 based on the image signal of G color of the normal light image, and for example, image signals of B color, R color, or all colors of RGB may be used. In this embodiment, since the image signal of B color of the normal light image includes the components of excited light 1 and 2 with strong emission intensity, and absorption of light by blood does not almost affect the image signal of R color, the image signal of G color is preferably used.

The compensation coefficients in FIG. 5 may be experimentally calculated in advance. For example, a scattering material (a solution having the same scattering characteristic as a living body, for example, an intralipid fluid solution 1%) and a fluorescent material (FAD, porphyrin (a concentration is about 10 μmol close to a concentration in a living body)) are put in a container, such as a dish, and normal light radiographing and self-fluorescent radiographing are performed while changing the concentration (hemoglobin concentration) in a range of 0 to 300 mg/dl. The relationship between the image signal of G signal of the normal light image and the fluorescence intensity of self-fluorescence is calculated, the relationship between the image signal of G color of the normal light image and the emission intensity of excited light 1 and 2 is calculated from the relationship between the fluorescence intensity and the emission intensity of excited light 1 and 2, and conversion is done from the calculated relationship such that the emission intensity becomes a given value. Thus, the graph of FIG. 5 can be created.

The compensation coefficients corresponding to the image signal of G color of the normal light image may be calculated using the compensation coefficient table which stores the compensation coefficients a and b corresponding to the image signal of G color of the normal light image, or an enumeration function of compensation coefficients, or the like may be used instead of the compensation coefficient table.

Next, the action of the endoscope diagnostic apparatus 10 will be described with reference to conceptual diagrams of FIGS. 6 and 7.

In the normal light observation mode, the laser light source LD1 is turned off and the laser light source LD2 is turned on under the control of the light source control unit 22. Laser light with the center wavelength of 445 nm emitted from the laser light source LD2 is irradiated onto the fluorescent substances 54A and 54B, and white light is emitted from the fluorescent substances 54A and 54B. As shown in FIG. 7, white light emitted from the fluorescent substances 54A and 54B is irradiated onto the subject, reflected light of white light is received by the imaging element 58A (normal sensor), and an normal light image including image signals of R, G, and B channels is imaged. The normal light image is color-displayed based on the image signals of the B, G, and R channels (normal light image processing).

Figure 6:
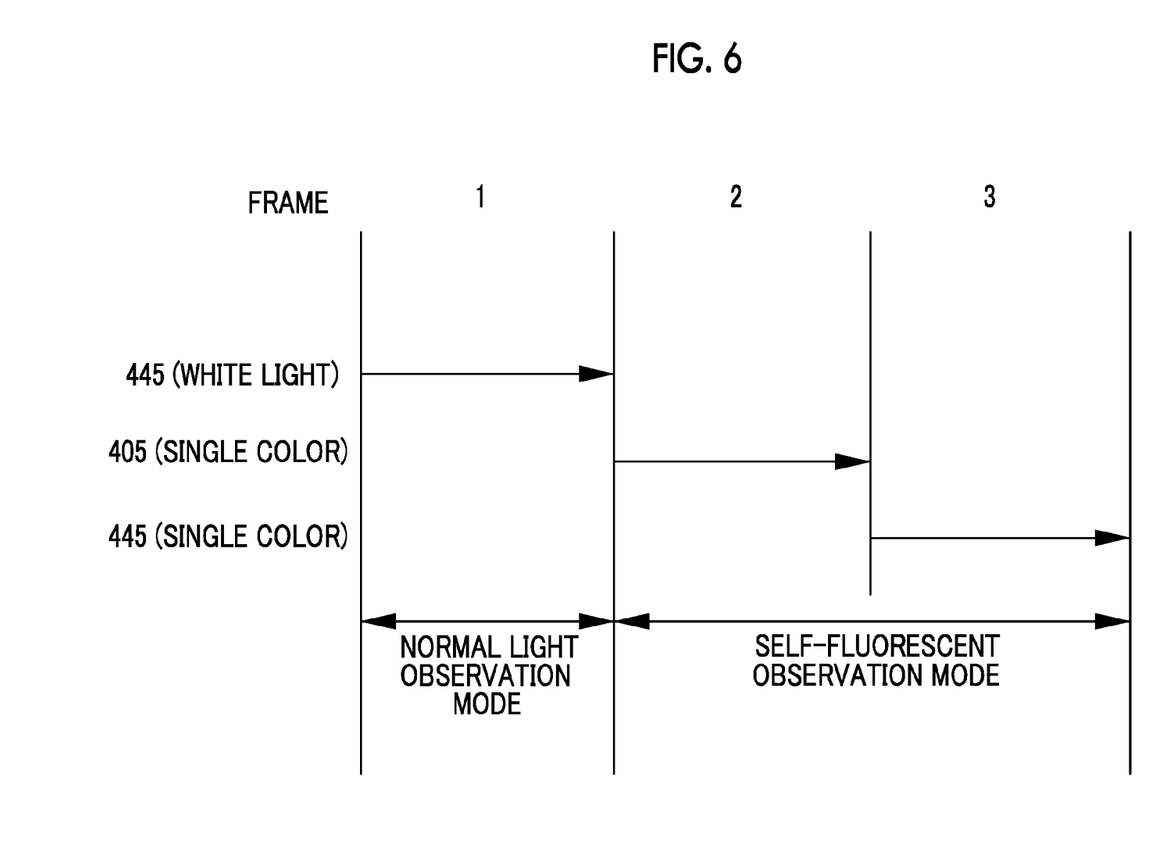
FIG. 6 is a conceptual diagram showing the action of the endoscope diagnostic apparatus shown in FIG. 1.
Figure 7:
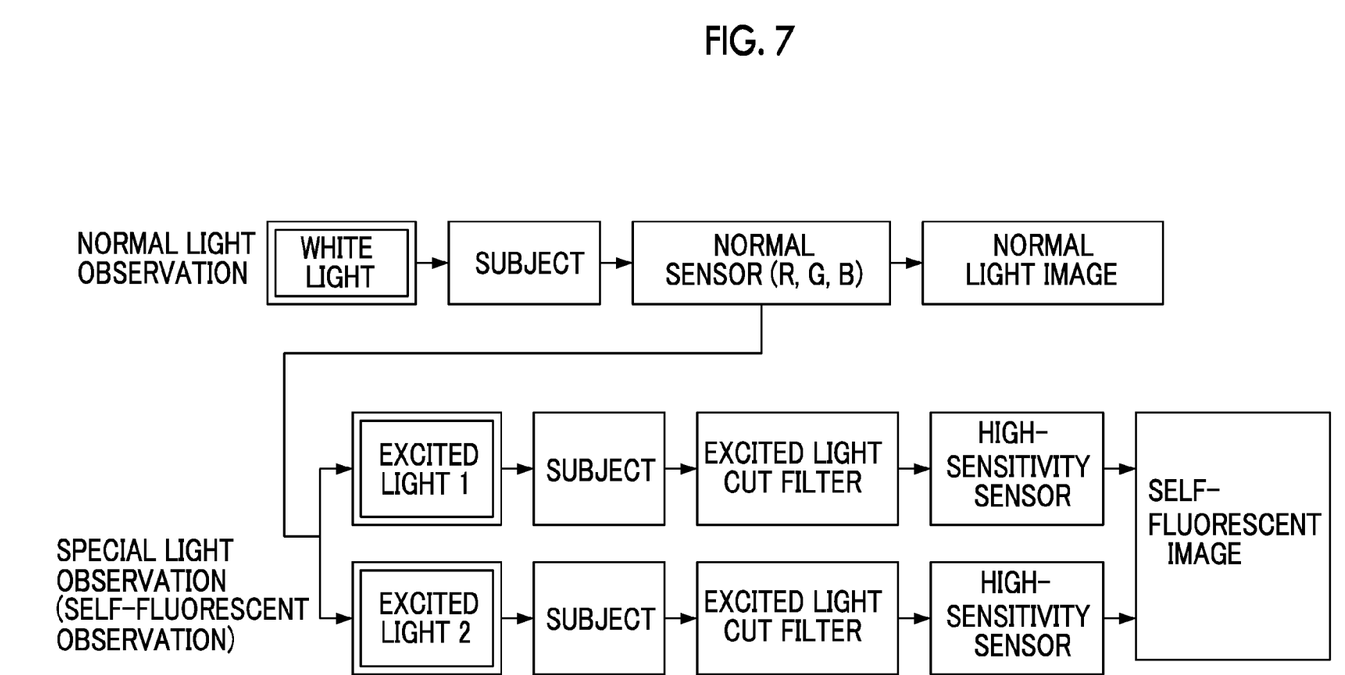
FIG. 7 is a conceptual diagram showing processing in a normal light observation mode and a self-fluorescent observation mode in the endoscope diagnostic apparatus shown in FIG. 1.

In the self-fluorescent observation mode, as shown in FIG. 6, for example, imaging is repeated in terms of three frames. Of the three frames, the first frame is the same observation mode as the normal light observation mode, and the second and third frames are an observation mode intrinsic to the self-fluorescent observation mode.

First, in the normal light observation mode of the first frame, as described above, the normal light image including the image signals of the R, G, and B channels is image. The normal light image signal is stored in the storage unit 72 under the control of the control unit 68.

After the normal light image is imaged, for example, the compensation coefficients a and b corresponding to the image signal of the G channel of the normal light image are calculated from the compensation coefficient table of the relationship shown in the graph of FIG. 5 under the control of the light source control unit 22. The ratios of the emission intensity of excited light 1 and the emission intensity of excited light 2 are compensated using the calculated compensation coefficients a and b so as to exclude the influence of absorption of light by blood in each kind of excited light 1 and 2.

Accordingly, the influence of absorption of light by blood can be excluded in the emission intensity of excited light 1 and 2. As a result, since the fluorescence intensity of self-fluorescence does not change depending on the blood volume of the subject, thereby obtaining self-fluorescent images, in which the influence of absorption of light by blood is excluded, in the subsequent second and third frames.

Subsequently, in the self-fluorescent observation mode of the second frame, the laser light source LD1 is turned on and the laser light source LD2 is turned off under the control of the light source control unit 22. As shown in FIG. 7, excited light 1 with the center wavelength 405 nm emitted from the laser light source LD1 is irradiated onto the subject, self-fluorescence emitted from the subject is received by the imaging element 58B (high-sensitivity sensor), and the self-fluorescent image 1 is imaged. The self-fluorescent image signal 1 is stored in the storage unit 72 under the control of the control unit 68.

As described above, a filter which cuts excited light 1 and 2 is provided in the imaging element 58B. For this reason, excited light 1 with the center wavelength of 405 nm is cut, and self-fluorescence in a wavelength range of 500 nm to 700 nm is imaged by the imaging element 58B.

Subsequently, in the self-fluorescent observation mode of the third frame, the laser light source LD1 is turned off and the laser light source LD2 is turned on under the control of the light source control unit 22. As shown in FIG. 7, excited light 2 with the center wavelength of 445 nm emitted from the laser light source LD2 is irradiated onto the subject, self-fluorescence emitted from the subject is received by the imaging element 58B (high-sensitivity sensor), and the self-fluorescent image 2 is imaged. The self-fluorescent image signal 2 is stored in the storage unit 72 under the control of the control unit 68.

Similarly, excited light 2 with the center wavelength of 445 nm is cut, and self-fluorescence in a wavelength range of 500 nm to 700 nm is imaged by the imaging element 58B.

In the self-fluorescent image processing unit 70B, the normal light image corresponding to the normal light image signal and the self-fluorescent images 1 and 2 stored in the storage unit 72 are combined, and the combined image of both images is displayed on the display device 18. In regard to the self-fluorescent images 1 and 2, the image signal of the self-fluorescent image 2 is allocated to the G channel, the image signal of the self-fluorescent image 1 is allocated to the R channel and the B channel under the control of the control unit 68, and the self-fluorescent images 1 and 2 are displayed on the display device 18 in a pseudo color manner (self-fluorescent image processing).

FAD and porphyrin described above are self-fluorescent materials which are correlated with a tumor. FAD has a characteristic in which light in a wavelength range of about 270 to 540 nm is absorbed, and porphyrin has a characteristic in which light in a wavelength range of about 340 to 450 nm is absorbed.

Accordingly, when excited light 1 with the center wavelength 405 nm is irradiated onto the subject as excited light for self-fluorescent observation, porphyrin is primarily excited, and self-fluorescence in a wavelength range of about 480 to 740 nm centering on a wavelength of about 630 nm is emitted from the region to be observed onto which excited light 1 is irradiated. When excited light 2 with the center wavelength of 445 nm is irradiated onto the subject as excited light for self-fluorescent observation, FAD is primarily excited, and self-fluorescence in a wavelength range of about 480 to 720 nm centering on a wavelength of about 550 nm is emitted from the region to be observed onto which excited light 2 is irradiated.

In the lesion part, the fluorescence intensity of FAD becomes weaker and the fluorescence intensity of porphyrin becomes stronger than the normal part thereof. Accordingly, a difference in the fluorescence intensity between FAD and porphyrin is captured, thereby distinguishing the normal part and the lesion part (reference: Tamura, Mamoru, "Series/Photobiology Vol. 6 Photomedicine Diagnosis", edited by Photobiology Association of Japan, Kyoritsu Shuppan Co., Ltd., Mar. 18, 2001).

Figure 8:
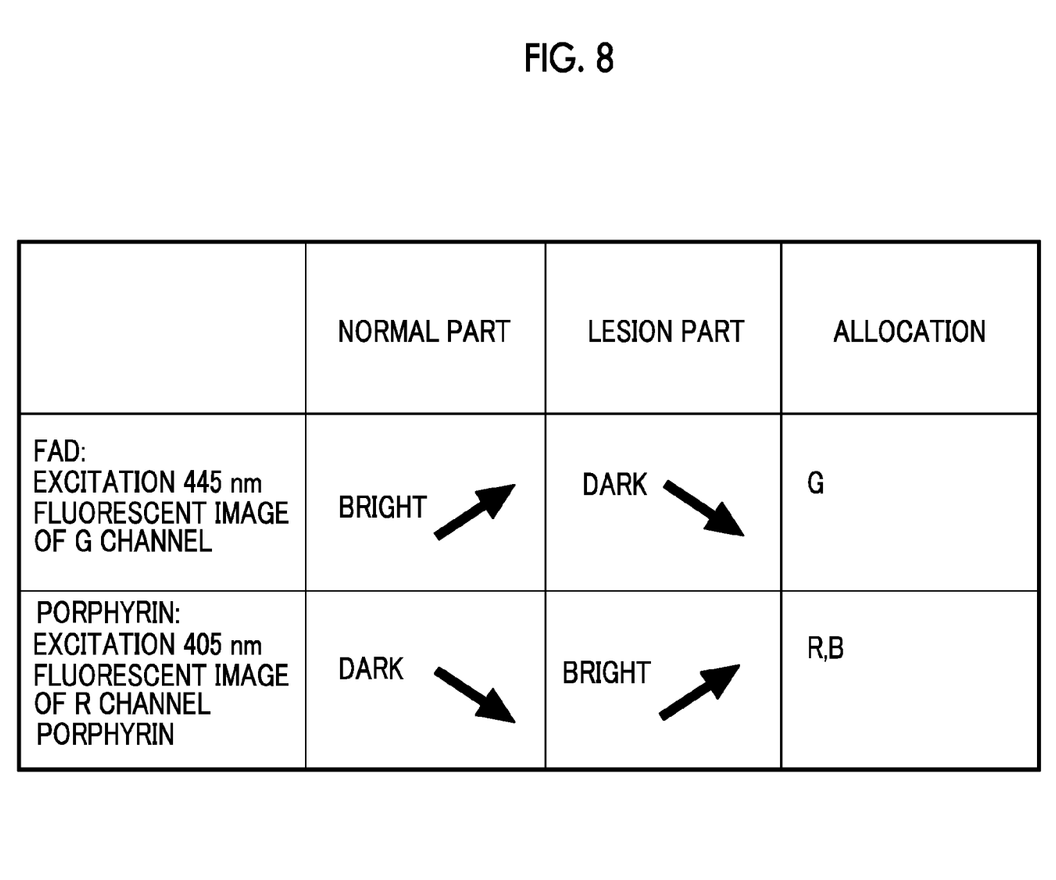
FIG. 8 is a table showing the fluorescence intensity of a normal part and a lesion part of FAD and porphyrin.

That is, as shown in FIG. 8, in the normal part, while the fluorescence intensity of FAD becomes stronger, the fluorescence intensity of porphyrin becomes weak. In the lesion part, a reverse relationship is established. As described above, in the endoscope diagnostic apparatus 10, the image signal of the self-fluorescent image 2 is allocated to the G channel, the image signal of the self-fluorescent image 1 is allocated to the R channel and the B channel, and pseudo color display is performed. For this reason, in the self-fluorescent images which are displayed by the endoscope diagnostic apparatus 10 in a pseudo color manner, the normal part is expressed with green and the lesion part is expressed with magenta. Meanwhile, the contrast of the lesion part becomes stronger than a single self-fluorescent image obtained by imaging self-fluorescence emitted from each of FAD and porphyrin, making it easy to recognize the lesion part.

As described above, in the endoscope diagnostic apparatus 10, the emission intensity of excited light 1 and 2 is compensated using the compensation coefficients a and b corresponding to the image signal of G color of the normal light image, thereby obtaining self-fluorescent images with no influence of absorption of light by blood.

In the self-fluorescent observation mode, it is not necessary to repeatedly perform imaging in terms of three frames. In the self-fluorescent observation mode, it is not necessary that laser light with a center wavelength of 405 nm and laser light with a center wavelength of 445 nm are sequentially irradiated. For example, these kinds of laser light may be irradiated simultaneously in one frame. When a self-fluorescent image is displayed in a pseudo color manner, to which color channel an image signal of a channel of a certain color is allocated is arbitrary. The self-fluorescent material is not limited to porphyrin and FAD.

The invention is basically as follows.

Although the present invention has been described in detail, the present invention is not limited to the foregoing embodiment, and various improvements or modifications may be of course made without departing from the scope of the present invention.

What is claimed is:

1. An endoscope diagnostic apparatus comprising:
   a light source unit which emits white light and two or more kinds of excited light with different center wavelengths for emitting two or more kinds of self-fluorescence from a self-fluorescent material included in a region to be observed of a subject;
   an imaging unit which, when white light is irradiated onto the region to be observed of the subject from the light source unit, receives reflected light of white light from the region to be observed of the subject to image a normal light image, and when the two or more kinds of excited light are irradiated onto the region to be observed of the subject from the light source unit, receives self-fluorescence emitted from the self-fluorescent material included in the region to be observed of the subject to image self-fluorescent images; and
   a light source control unit configured to:
   calculate the amount of absorption of the two or more kinds of excited light by blood;
   determine a compensation coefficient for each of the two or more kinds of excited light;
   compensate the ratios of emission intensity of the two or more kinds of excited light using the determined compensation coefficients so as to exclude the influence of absorption of light by blood in each of the two or more kinds of excited light.

2. The endoscope diagnostic apparatus according to claim 1,
   wherein the light source control unit compensates the ratios of emission intensity of the two or more kinds of excited light such that, as the image signal of the normal light image becomes smaller than a predetermined value, the emission intensity of excited light with a large amount of absorption of light by blood is greater than the emission intensity of excited light with a smaller amount of absorption of light by blood than excited light with a large amount of absorption of light by blood.

3. The endoscope diagnostic apparatus according to claim 2,
   wherein, when the image signal of the normal light image is greater than a predetermined value, the light source control unit compensates the ratios of emission intensity of the two or more kinds of excited light such that the ratios of emission intensity of the two or more kinds of excited light are the same.

4. The endoscope diagnostic apparatus according to claim 3,
   wherein the light source control unit has a compensation coefficient table which stores the compensation coefficients of the emission intensity of the two or more kinds of excited light corresponding to the image signal of the normal light image, and calculates the compensation coefficients of the emission intensity of the two or more kinds of excited light corresponding to the image signal of the normal light image using the compensation coefficient table.

5. The endoscope diagnostic apparatus according to claim 2,
   wherein the light source control unit has a compensation coefficient table which stores the compensation coefficients of the emission intensity of the two or more kinds of excited light corresponding to the image signal of the normal light image, and calculates the compensation coefficients of the emission intensity of the two or more kinds of excited light corresponding to the image signal of the normal light image using the compensation coefficient table.

6. The endoscope diagnostic apparatus according to claim 2,
   wherein the light source unit includes first excited light with a center wavelength of 405 nm and second excited light with a center wavelength of 445 nm as the two or more kinds of excited light.

7. The endoscope diagnostic apparatus according to claim 6,
   wherein the light source unit comprises a laser light source which emits the first excited light and the second excited light.

8. The endoscope diagnostic apparatus according to claim 7,
   wherein the light source control unit compensates the ratios of the emission intensity of the two or more kinds of excited light based on an image signal of green of the normal light image.

9. The endoscope diagnostic apparatus according to claim 6,
   wherein the light source control unit compensates the ratios of the emission intensity of the two or more kinds of excited light based on an image signal of green of the normal light image.

10. The endoscope diagnostic apparatus according to claim 2,
    wherein the imaging unit comprises a first imaging element which images the normal light image, a color filter which is disposed on the optical path of the first imaging element, and has a spectral transmission characteristic for transmitting light in a wavelength range according to blue, green, and red, a second imaging element which has sensitivity higher than the first imaging element imaging the normal light image, and a filter which is disposed on the optical path of the second imaging element, and does not transmit light in the wavelength range of the two or more kinds of excited light.

11. The endoscope diagnostic apparatus according to claim 3,
wherein the light source unit includes first excited light with a center wavelength of 405 nm and second excited light with a center wavelength of 445 nm as the two or more kinds of excited light.

12. The endoscope diagnostic apparatus according to claim 3,
wherein the imaging unit comprises a first imaging element which images the normal light image, a color filter which is disposed on the optical path of the first imaging element, and has a spectral transmission characteristic for transmitting light in a wavelength range according to blue, green, and red, a second imaging element which has sensitivity higher than the first imaging element imaging the normal light image, and a filter which is disposed on the optical path of the second imaging element, and does not transmit light in the wavelength range of the two or more kinds of excited light.

13. The endoscope diagnostic apparatus according to claim 1,
wherein the light source control unit has a compensation coefficient table which stores the compensation coefficients of the emission intensity of the two or more kinds of excited light corresponding to the image signal of the normal light image, and calculates the compensation coefficients of the emission intensity of the two or more kinds of excited light corresponding to the image signal of the normal light image using the compensation coefficient table.

14. The endoscope diagnostic apparatus according to claim 13,
wherein the light source unit includes first excited light with a center wavelength of 405 nm and second excited light with a center wavelength of 445 nm as the two or more kinds of excited light.

15. The endoscope diagnostic apparatus according to claim 1,
wherein the light source unit includes first excited light with a center wavelength of 405 nm and second excited light with a center wavelength of 445 nm as the two or more kinds of excited light.

16. The endoscope diagnostic apparatus according to claim 15,
wherein the light source unit comprises a laser light source which emits the first excited light and the second excited light.

17. The endoscope diagnostic apparatus according to claim 16,
wherein the light source control unit compensates the ratios of the emission intensity of the two or more kinds of excited light based on an image signal of green of the normal light image.

18. The endoscope diagnostic apparatus according to claim 15,
wherein the light source control unit compensates the ratios of the emission intensity of the two or more kinds of excited light based on an image signal of green of the normal light image.

19. The endoscope diagnostic apparatus according to claim 1,
wherein the imaging unit comprises a first imaging element which images the normal light image, a color filter which is disposed on the optical path of the first imaging element, and has a spectral transmission characteristic for transmitting light in a wavelength range according to blue, green, and red, a second imaging element which has sensitivity higher than the first imaging element imaging the normal light image, and a filter which is disposed on the optical path of the second imaging element, and does not transmit light in the wavelength range of the two or more kinds of excited light.

* * * * *